(12) United States Patent
Lamanna et al.

(10) Patent No.: US 6,580,006 B1
(45) Date of Patent: Jun. 17, 2003

(54) CATALYTIC PROCESS FOR PREPARING PERFLUOROETHANESULFONYL FLUORIDE AND/OR PERFLUORODIETHYLSULFONE

(75) Inventors: William M. Lamanna, Stillwater, MN (US); Michael D. Barrera, Oakdale, MN (US); Gerald L. Bauer, Hudson, WI (US); Yuri Cheburkov, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/137,165

(22) Filed: May 2, 2002

(51) Int. Cl.[7] .................................. C07C 309/00
(52) U.S. Cl. ................................ 562/825; 568/35
(58) Field of Search ...................... 562/825; 568/27, 568/35

(56) References Cited

U.S. PATENT DOCUMENTS

| | | | |
|---|---|---|---|
| 2,519,983 A | 8/1950 | Simons | |
| 3,542,864 A | 11/1970 | Koshar | |
| 3,920,738 A | * 11/1975 | Martin | 562/825 |
| 4,269,790 A | * 5/1981 | de Vries | 562/825 |
| 5,206,440 A | * 4/1993 | Beckerbauer et al. | 568/35 |
| 5,318,674 A | * 6/1994 | Behr et al. | 205/430 |
| 5,637,663 A | 6/1997 | Anolick et al. | |
| 5,780,682 A | 7/1998 | Zavilla et al. | |
| 6,372,829 B1 | 4/2002 | Lamanna et al. | |

FOREIGN PATENT DOCUMENTS

GB 1189561 4/1970

OTHER PUBLICATIONS

CA:95:132234 abs of Zhurnal Organicheskoi Khimii by Radchenko et al 17(3) pp 500–3 1981.*
CA:98:125354 abs of Inorganic Chemistry by Imagawa 22(6) pp 969–71 1983.*
Article: Graham, "Fluoride Ion Initiated Reactions of Perfluoro α–Olefins. I. Reaction of the Pentafluoroethyl Carbanion with Tetrafluoroethylene," *J. Org. Chem.*, vol. 31, Mar., 1996, pp. 955–959.
Article: Temple, "The Reaction of Sulfuryl Fluoride and Sulfonyl Fluorides with Fluoro Olefins," *J. Org. Chem.*, vol. 33, No. 1, Jan., 1968, pp. 344–346.
Article: Gokel et al., "Principles and Synthetic Applications in Crown Ether Chemistry," *Synthesis*, (1976), pp. 168–184.

* cited by examiner

*Primary Examiner*—Jean F. Vollano
(74) *Attorney, Agent, or Firm*—Lisa M. Fagan

(57) ABSTRACT

The present invention provides a catalytic process for preparing perfluoroethanesulfonyl fluoride and/or perfluorodiethylsulfone using a two-part catalytic process comprising a metal fluoride and a crown ether.

21 Claims, 7 Drawing Sheets

CATALYTIC PROCESS FOR PREPARING PERFLUOROETHANESULFONYL FLUORIDE AND/OR PERFLUORODIETHYLSULFONE

FIELD OF THE INVENTION

This invention relates to an improved process for manufacturing perfluoroethanesulfonyl fluoride and/or perfluorodiethylsulfone. More particularly, the present invention relates to using a two-part catalytic system for preparing perfluoroethanesulfonyl fluoride and/or perfluorodiethylsulfone.

BACKGROUND OF INVENTION

Perfluoroethanesulfonyl fluoride (PESF) and perfluorodiethylsulfone (PDES) may be used in a variety of applications. For example perfluoroethanesulfonyl fluoride is an intermediate in the manufacture of lithium bisperfluoroethanesulfonylimide (the BETI salt, available from 3M Company as FC-130), which is used as an electrolyte commercially in rechargeable lithium batteries. PESF may also be used as an intermediate in the manufacture of perfluoroethanesulfonate and various methide anions such as $^-C(SO_2C_2F_5)_3$. Perfluorodiethylsulfone may be used as a solvent, heat exchange fluid or as a reactive intermediate in the manufacture of perfluoroethanesulfonate and perfluoroethanesulfonyl amide. Perfluorodiethylsulfone may also be used as an initiator for preparing amorphous copolymers of tetrafluoroethylene (TFE) with hexafluoropropylene (HFP). (See, U.S. Pat. No. 5,637,663).

Fluoride catalyzed reactions of fluoroolefins, such as TFE and HFP, with $SO_2F_2$ to produce perfluoroethanesulfonyl fluoride (PESF), perfluorodiethylsulfone (PDES), and perfluoro-iso-propanesulfonyl fluoride, respectively, are known in the art. Whereas the reaction of HFP with $SO_2F_2$ to produce perfluoro-iso-propanesulfonyl fluoride proceeds readily under moderate reaction conditions (50–100° C.) using conventional one-part metal fluoride catalysts (e.g., KF and CsF), the corresponding metal fluoride-catalyzed reaction of TFE with $SO_2F_2$ to produce PESF and PDES is relatively sluggish. Generally, the latter reaction requires high temperatures ($\geq 100°$ C.), long reaction times and/or very high catalyst loadings to achieve reasonable conversions or practical rates of reaction.

For example, in J. Org. Chem., 33(1), 344 (1968) and GB Patent No. 1,189,561, S. Temple describes the catalytic reaction of TFE with $SO_2F_2$ using CsF as the catalyst and diglyme as the solvent to produce PDES. Under 100° C., this reaction is impractically slow. High temperatures (and pressures) and high catalyst loadings are required to achieve practical rates of conversion.

U.S. Pat. No. 3,542,864 ((Koshar) discloses the reaction of TFE with $SO_2F_2$ in a solvent such as dimethylformamide or acetonitrile using an alkali metal fluoride such as CsF to produce PESF. But at moderate reaction temperatures (and pressures) this reaction is impractically slow.

U.S. Pat. No. 5,780,682 (Zavilla et al.) discloses the preparation of fluorinated alkyl sulphonyl halides by reacting a fluorinated unsaturated hydrocarbon with a sulfuryl halide. The reaction is carried out in the presence of at least a catalytic amount of fluoride in a solvent comprising an alkyl sulfonyl or alkylsulfoxide compound. No reactions of TFE are exemplified.

Thus, for economic reasons and due to pressure limitations of process equipment used in large scale manufacturing, the need exists for a more active catalyst system that accelerates the rate of reaction of TFE with $SO_2F_2$ and allows preparation of PESF and PDES at lower temperatures and pressures and at a reasonable rate while also providing control of the PESF/PDES product distribution.

SUMMARY OF THE INVENTION

The present invention provides a process for preparing perfluoroethanesulfonyl fluoride and/or perfluorodiethylsulfone using a two-part catalytic system. Advantageously, the catalytic system of the present invention provides higher catalytic activity and significantly faster rates of reaction under a given set of reaction conditions versus known one-part catalysts.

The present invention comprises a method of preparing perfluoroethanesulfonyl fluoride and/or perfluorodiethylsulfone from tetrafluoroethylene (TFE) and sulfuryl fluoride ($SO_2F_2$). The present invention comprises a catalytic process for the preparation of perfluoroethanesulfonyl fluoride and/or perfluorodiethylsulfone comprising the steps of:

(a) reacting in the presence of a two-part catalyst system in a polar aprotic organic solvent:
  (i.) tetrafluoroethylene, and
  (ii.) sulfuryl fluoride;
    wherein said two-part catalyst system comprises a metal fluoride and a crown ether; and (b) recovering perfluoroethanesulfonyl fluoride or perfluorodiethylsulfone, or a mixture thereof.

Another embodiment of the present invention is a process further comprising combining an immiscible, highly fluorinated co-solvent with the polar aprotic organic solvent.

DETAILED DESCRIPTION OF ILLUSTRATIVE EMBODIMENTS

Figure 1:
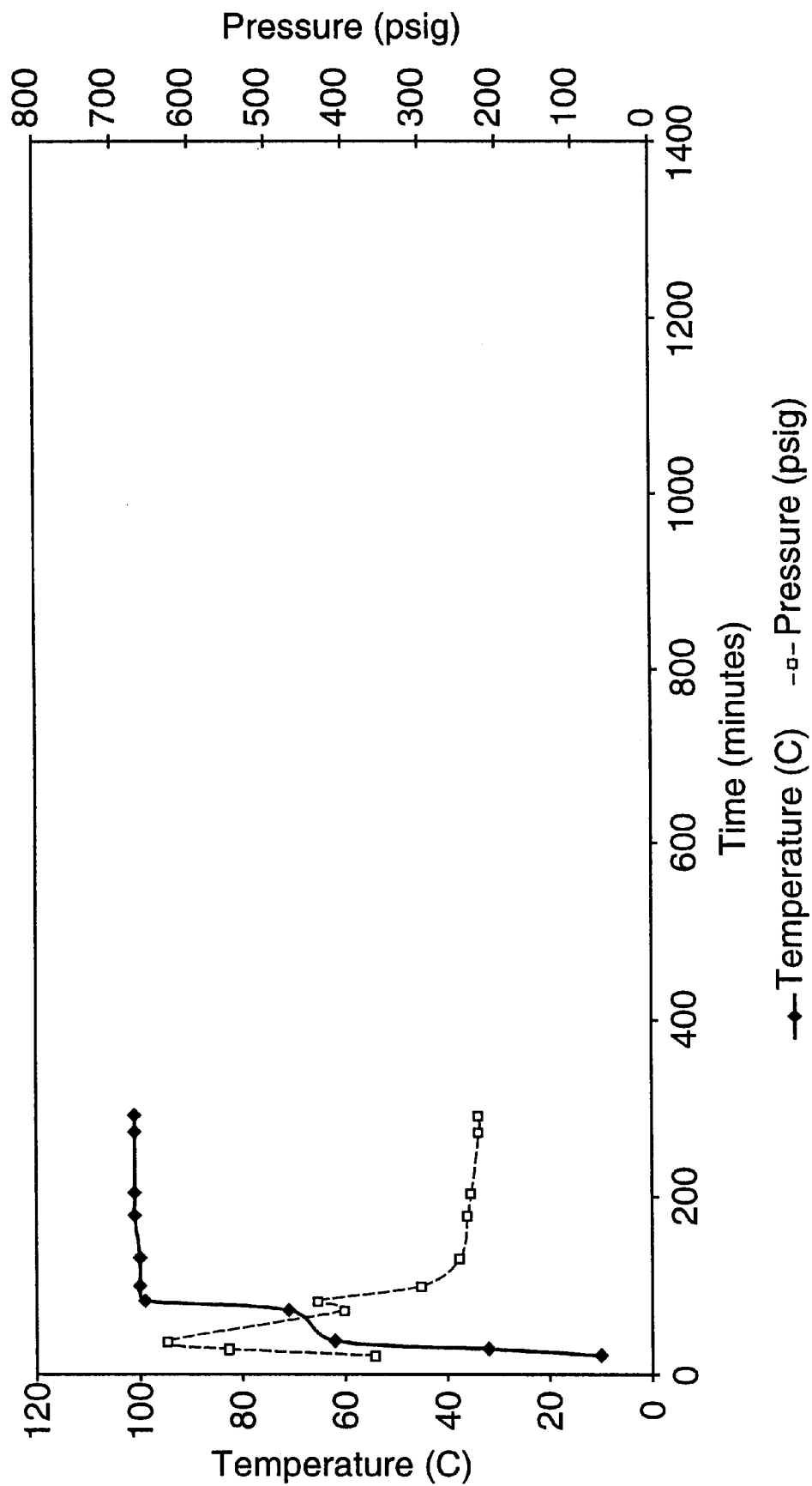
FIG. 1 is a graph of reaction temperature and pressure versus time for Example 14.

The present invention provides a process for manufacturing perfluoroethanesulfonyl fluoride and/or perfluorodiethylsulfone using a two-part catalyst system. The process involves the fluoride-catalyzed reaction of tetrafluoroethylene with sulfuryl fluoride. Overall, the reaction can be set forth as follows:

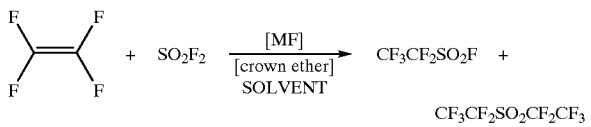

The reaction proceeds according to the following steps, wherein the crown ether co-catalyst serves to activate the metal fluoride catalyst, MF, presumably by complexing the metal cation and thereby generating a more reactive form of fluoride anion, F⁻.

Step 1

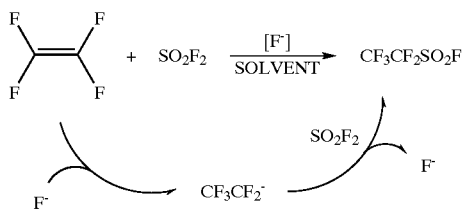

Step 2

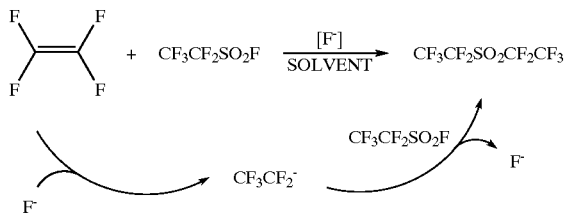

In the case where PDES is the desired product, Step 2 can be performed independent of Step 1 by using TFE and PESF as the reactants. Step 2 can also be performed using a different fluoroalkanesulfonyl fluoride, $R_fSO_2F$ (where $R_f$ is a fluorinated alkyl having from 1 to 10 carbon atoms) as a reactant instead of $CF_3CF_2SO_2F$. This substitution produces a mixed fluoroalkyl sulfone containing a single perfluoroethyl group and a second fluoroalkyl chain.

Sulfuryl fluoride is available commercially from Dow-AgroSciences (Indianapolis, Ind.). Tetrafluoroethylene is available commercially from Daikin (Decatur, Ala.) or 3M Company (St. Paul, Minn.).

Catalyst System

The present invention provides a two-part catalyst system comprising a metal fluoride and a crown ether. This catalyst system provides higher catalytic activity and significantly faster rates of reaction under a given set of reaction conditions than other known catalysts. For example, the two-part catalyst system of the present invention comprising KF and 18-crown-6 in a polar aprotic organic solvent provides rates of reaction between TFE and $SO_2F_2$ that are at least 2 to 5 times faster than CsF under similar conditions and catalyst loadings, regardless of solvent used with the CsF.

The higher catalytic activity associated with the two-part catalyst system of the present invention provides advantages including, but not limited to, processing advantages such as lower temperature operation, lower pressure operation, decreased cycle times, lower processing costs, greater safety, and fewer by-products. Additionally, the two-part catalyst system of the present invention can be reused multiple times. Therefore, the reactor productivity is increased and the cost of the relatively expensive crown ether co-catalyst can be mitigated. For example, in one embodiment of the present invention, a two-part catalyst system comprising KF and 18-crown-6 in dimethyl formamide can be reused a total of at least seven times without an unacceptable loss in catalytic activity.

Particularly suitable metal fluorides include alkali metal fluorides, including but not limited to: NaF, KF, and CsF. Preferably, the metal fluoride is KF. KF is a less costly alternative to CsF and is also easier to dry and handle in anhydrous form. Suitable metal fluorides are available commercially from Sigma-Aldrich (Milwaukee, Wis.).

The crown ether co-catalyst can be any crown ether having a high binding constant for the metal cation of the metal fluoride catalyst (i.e., stability constant $Log_{10}K$ (in liters/mole at 25° C.) greater than 2, preferably greater than 4). Suitable crown ethers are available commercially from Sigma-Aldrich or Parish Chemical (Orem, Utah).

Suitable crown ethers include the general classes of monocyclic and bicyclic crowns (or cryptates) described by Gokel and Durst in *Synthesis*, 168 (1976). Specific examples include, but are not limited to: 18-crown-6, dibenzo-18-crown-6, dicyclohexane-18-crown-6, and dibenzo-24-crown-8. When KF is used as a catalyst, 18-crown-6 is a preferred co-catalyst.

Generally, the metal fluoride catalyst and the crown ether co-catalyst are each present at between 1 to 10 wt % in the polar aprotic solvent. The crown ethers are generally completely soluble in the polar aprotic solvent at these levels, whereas the metal fluorides may be soluble, but are usually only very slightly soluble, even in the presence of the crown ether. Thus the metal fluoride catalyst may be only partially dissolved in the polar aprotic solvent during the course of the catalytic reaction. It is preferable from the standpoint of efficiency and cost to maximize the number of catalytic turnovers per mole of catalyst and co-catalyst. Therefore, the combined catalyst charge (metal fluoride+crown ether) is generally less than 20%, preferably less than 5% and most preferably less than 1% of the total combined $SO_2F_2$ plus TFE charge (by wt.) used in a run or series of runs (if the catalyst is reused). The mole ratio of metal fluoride to crown ether may vary between 10:1 and 1:10, but is preferably between 2:1 and 1:2. The preferred mole ratio of TFE to $SO_2F_2$ depends on the desired product and mode of operation, but is generally 1:10 to 10:1 and typically between 2:1 and 1:2.

Polar Aprotic Organic Solvent

The two-part catalyst system is dissolved or suspended in a polar aprotic organic solvent. A polar solvent is defined herein as one that has a dielectric constant greater than 25 at room temperature. An aprotic solvent is defined herein as a solvent that does not donate protons readily. These solvents have no active hydrogen atom (e.g., a hydroxy, carboxy, sulfoxy, or amino functionality).

Solvents useful in the present invention generally have a dielectric constant at room temperature greater than 25, preferably greater than 30.

The solvents of the present invention are generally liquid at temperatures less than 50° C.

Examples of suitable polar aprotic organic solvents include, but are not limited to, acetonitrile, dimethylformamide (DMF), dimethylacetamide (DMA), sulfolane, dimethylsulfoxide (DMSO), propylene carbonate (PC), 1,3-dimethyl imidazolidin-2-one (DMEU), 1,3-dimethyl-2-oxohexahydropyrimidine (DMPU), gamma-butyrolactone, nitromethane, 1-methyl-2-pyrrolidinone (NMP), dimethylsulfone, hexamethylphosphoramide (HMPA), and the like.

Co-solvent

An immiscible, highly fluorinated co-solvent may optionally be combined with the polar aprotic organic solvent. Immiscible is defined herein as forming a separate liquid phase with the polar aprotic solvent. Highly fluorinated is defined herein as having a F:H ratio greater than 3, preferably greater than 5. Preferably the highly fluorinated co-solvent is perfluorinated or contains only Cl and F bound to carbon. Most preferably, the highly fluorinated co-solvent is perfluorinated. The incorporation of this co-solvent improves the PESF yield and selectivity toward PESF versus perfluorodiethylsulfone. In addition, the presence of this co-solvent suppresses the overall vapor pressure of the reaction mixture (i.e., lowers operating pressures) without adversely affecting the rate of reaction.

Highly fluorinated co-solvents suitable for the present invention include, but are not limited to, perfluorocarbons such as perfluorooctane and perfluorohexane, perfluorinated tertiary amines such as perfluorotributyl amine and perfluorotriamylamine, perfluorinated ether-amines such as perfluoro-N-methyl morpholine, cyclic and acyclic perfluorinated ethers such as $C_4F_9$-c-$C_4F_7O$, and perfluoropolyethers, and various hydrofluorocarbons and chlorofluorocarbons. In addition, the liquid by-product, PDES, can be used as the highly fluorinated co-solvent for the process to manufacture PESF.

Inhibitor

Optionally, a sufficient amount of inhibitor may be present to prevent free radical polymerization of the tetrafluoroethylene. An example of a suitable inhibitor is limonene.

Catalytic Process

The catalytic process of the present invention may be performed in any suitable reaction vessel, although a pressurized vessel is preferred. The process may be carried out by adding the two-part catalyst system to the polar aprotic organic solvent (and optionally an immiscible highly fluorinated co-solvent). The reactor contents are then agitated at a temperature ranging from 0 to 150° C., preferably from 50 to 100° C. Sulfuryl fluoride may be batch charged or gradually added. The TFE amount is preferably added gradually to the reactor in a continuous or semi-continuous manner after the $SO_2F_2$ has been charged or simultaneously with the $SO_2F_2$. The desired product(s), PESF and/or PDES may then be recovered by distillation from the reaction mixture or by draining the immiscible lower liquid product phase from the reactor.

In another embodiment of the present invention, the two-part catalyst system may be reused two or more times by recharging the TFE and $SO_2F_2$ starting materials after product from an earlier run has been selectively removed and collected.

In yet another embodiment, the catalytic process may be conducted in a continuous manner by employing continuous product removal as the starting materials are being fed.

The catalytic process of the present invention can be tailored to produce primarily PESF or PDES. The reactant stoichiometry, reaction conditions, solvent, co-solvent, and percent conversion can be altered to favor either PESF or PDES. Generally, PESF is favored by a high $SO_2F_2$:TFE ratio, (greater than 1.0), low reaction temperatures, (less than 80° C.), low percent conversions (less than 90% of limiting reagent), and the use of a highly fluorinated co-solvent. The opposite is generally preferable for the manufacture of primarily PDES.

The catalytic process of the present invention is sensitive to moisture. Water tends to reduce catalytic activity and can, at sufficiently high levels, completely de-activate the catalyst system. Thus, precautions to exclude moisture from all reaction components, including the two-part catalyst system, polar aprotic organic solvent, TFE and $SO_2F_2$ reactants, and the reactor itself are desirable. Standard techniques known in the art for drying and handling common anhydrous materials and for pre-drying a reactor are suitable. Generally, commercially available anhydrous solvents, TFE, $SO_2F_2$, and crown ethers are adequately dry as purchased for use in the present process, although precautions are recommended to avoid additional moisture uptake. Metal fluorides generally require vacuum drying at elevated temperatures (100–180° C.) prior to use in the present process.

For example, a metal fluoride, such as KF, can be dried in a vacuum oven at 160° C. and $10^{-2}$ Torr and then stored and dispensed in a nitrogen-filled dry box. Crown ethers can be purchased, stored, and dispensed in a dry box without further treatment. Solvents can be purchased in anhydrous form and either stored over 3A molecular sieves or used without further treatment.

In one embodiment of the present invention, a 100 mL Parr reactor is dried by rinsing with acetone after aqueous clean-up and then heating for at least a few hours at 100° C. prior to evacuation in a dry box antechamber. The reactor is then loaded with the two-part catalyst system and polar aprotic organic solvent in the dry box and sealed. $SO_2F_2$ and TFE are then charged to the reactor in the desired amounts from pressurized gas cylinders.

In another embodiment of the present invention, a 1 gallon (3.8 liters) stainless steel pressure reactor is dried after aqueous clean-up using one or two acetone boil-outs followed by acetone discharge and vacuum drying at elevated temperature (approximately 80 to 100° C. and 1 to 10 Torr). Under standby conditions, the reactor is maintained under a nitrogen atmosphere and all reagents are charged to the reactor from a nitrogen-pressurized stainless steel cylinder that is precharged in a dry box with minimal or no exposure to ambient moisture. A column packed with carbon may optionally be used to scavenge the limonene inhibitor from the TFE.

In one embodiment of the present invention, PESF is made practically using the catalytic process of the present invention at a reaction temperature of about 70° C. and a maximum reaction pressure of about 240 psia (1.65 MPa). PESF and PDES yields of 75% and 15% respectively (based on $SO_2F_2$) are achieved with a solvent/catalyst mixture that includes an immiscible highly fluorinated co-solvent. The solvent/catalyst mixture is reused for at least 7 reactions before being replaced.

EXAMPLES

The following examples illustrate various specific features, advantages, and other details of the invention. The particular materials and amounts recited in these examples, as well as other conditions and details, should not be construed in a manner that would unduly limit the scope of this invention. All parts, percentages, and ratios are by weight unless otherwise specified.

As used in the examples that follow: "ppm" means parts per million, and the prefix "perfluoro" denotes substitution of all carbon-bonded hydrogen atoms by fluorine atoms.

Table of Components

| Component | Description | Available From |
|---|---|---|
| Tetrafluoroethylene | $CF_2=CF_2$ | DuPont, Wilmington, DE |
| Sulfuryl fluoride | $SO_2F_2$ | Dow AgroSciences, Indianapolis, IN |
| N,N-dimethyl-formamide | DMF, anhydrous (water < 0.005%) | Sigma-Aldrich, Milwaukee, WI |
| 18-crown-6 | 18-C-6 | Parish Chemical Company, Orem, UT |
| Potassium Fluoride, | KF, spray dried, oven dried at 160° C. and 0.01 Torr after purchase | Sigma-Aldrich |
| FC-1 | Mixture of perfluorinated amines, including $(C_5F_{11})_3N$ | Prepared by electrochemical fluorination of $(C_5H_{11})_3N$; see column 18, U.S. Pat. No. 2,519,983 |
| FLUORAD ™ FC43 | | 3M Company, St. Paul, MN |
| FLUORAD ™ FC3255 | | 3M |
| FLUORAD ™ FC-104 | | 3M |
| Cesium fluoride | CsF (anhydrous), oven dried at 160° C., 0.01 Torr after purchase | Sigma-Aldrich or ARC (Advanced Research Chemicals), Catoosa, OK |
| Sodium fluoride | NaF | Sigma-Aldrich |
| Dibenzo-18-crown-6 | DB-18-C-6 | Parish Chemical Company |
| Dicyclohexano-18-crown-6 | DC-18-C-6 | Parish Chemical Company |
| Trimethyl amine | $Me_3N$ | Sigma-Aldrich |
| 1,8-bis(dimethylamino)naphthalene | PROTON-SPONGE ™ | Sigma-Aldrich |
| Potassium iodide | KI | Sigma-Aldrich |
| Tetraethyleneglycol ether | Tetraglyme | Sigma-Aldrich |
| N,N-dimethylacetamide | DMA, anhydrous | Sigma-Aldrich |
| 2-methyoxyethyl ether | Diglyme, anhydrous | Sigma-Aldrich |
| Acetonitrile | $CH_3CN$, anhydrous | Sigma-Aldrich |
| 1,2-dichlorobenzene | o-DCB, anhydrous | Sigma-Aldrich |
| Tetramethylene sulfone | Sulfolane, 99% | Sigma-Aldrich |
| 1,3-dimethyl-3,4,5,6-tetrahydro-2(1H)-pyrimidinone | DMPU, 98% | Sigma-Aldrich |
| Propylene carbonate | PC, anhydrous | Sigma-Aldrich |
| Tetrabutylammonium bis(trifluoromethanesulfonyl)imide | $Bu_4N^+$ $-N(SO_2CF_3)_2$ | See synthesis of Compound 5, Columns 16–17, in U.S. Pat. No. 6,372,829 |
| Triethylamine trihydrofluoride | $Et_3N$-3HF | Sigma-Aldrich |
| Tetrakis(dimethylamino)ethylene | $(Me_2N)_2C=C(NMe_2)_2$, 97% | Sigma-Aldrich |

General Procedure

An oven-dried, 100 milliliter (mL), stainless steel Parr reactor, (Parr Instrument, Company, Moline, Ill.) equipped with a mechanical magnedrive stirrer, thermocouple probe, pressure gauge, and rupture disk, was transferred to a Vacuum Atmosphere's dry box maintained under a dry nitrogen atmosphere and charged with anhydrous metal fluoride catalyst (typically 0.5 to 2.0 grams (g)), crown ether co-catalyst (typically 0.5 to 2.0 grams, if present), and solvent (typically about 32 mL total). Once charging was complete, the reactor was assembled, all valves were closed, and the reactor was removed from the dry box, preweighed, and secured in the Parr reactor support stand with connections made to all plumbing, mechanical, and electrical peripherals. The reaction mixture was chilled to about −10 to −25° C. with stirring using a dry ice bath to cool the reactor body. While chilling the reactor, all gas lines were purged by repeated evacuation and back flush with house nitrogen to remove air. Sulfuryl fluoride from a tared cylinder was gradually charged to the chilled reactor with stirring while monitoring the weight change of the $SO_2F_2$ cylinder using a balance. Once charging was complete, the reactor was isolated by closing the inlet valve and the residual $SO_2F_2$ in the transfer line was eliminated by evacuation. The $SO_2F_2$ cylinder was disconnected from the gas inlet line and reweighed to obtain an accurate value for the total amount of $SO_2F_2$ charged (typically about 10 to 15 grams). Based upon the actual amount of $SO_2F_2$ charged, the number of grams of TFE required to give an equimolar amount was calculated.

While continuing to chill the reactor in dry ice, a tared cylinder containing limonene-inhibited TFE was connected to the gas inlet line that was then purged as before to remove air. While holding the reaction solution temperature at about 0 to 10° C., the reactor was gradually charged with approximately the calculated amount of TFE with stirring. Once the TFE was charged, the reactor gas inlet valve was closed, the transfer line was evacuated to eliminate residual TFE, and the TFE cylinder was disconnected and reweighed to get an accurate value for the actual amount of TFE added (typically about 10 to 15 grams, calculated by difference). The fully charged reactor was reweighed, and then the reaction temperature was rapidly stepped up in approximately 20° C. increments with stirring until a maximum temperature of about 100° C. or a maximum pressure of about 700 psi (4.82 MPa) was reached.

A record of reaction time, temperature, and pressure was made regularly because this data profile was useful in estimating and comparing rates of reaction.

Upon completion of the reaction, the reactor was cooled to approximately room temperature with stirring, all peripherals were disconnected, and the Parr reactor was reweighed to verify that no mass was lost (through leakage) during the reaction. While the reaction solution was at approximately room temperature, a small headspace vapor sample was removed by venting to a TEFLON™ bag equipped with a gas-tight valve. The headspace sample was analyzed by gas chromatography on a Supelco Carbopack C column (available from Supelco, Bellefonte, Pa.) to determine headspace composition, which provides a qualitative measure of percent conversion. A warm water bath was then applied to the reactor bottom and all volatiles were distilled from the reactor (through the gas inlet valve on the reactor head) between about 25 and about 60° C. (bath temperature) and collected in a tared dry ice trap. Once all volatiles were collected, the cold trap and reactor were reweighed to calculate the mass balance. The contents of the trap were allowed to warm to 0° C. while permitting the low boiling volatiles to vent through an oil bubbler. The vent gasses emitted from the trap, the liquid remaining in the trap after warming to 0° C., and the residual nonvolatile liquid in the Parr reactor were all analyzed by GC, as before, to estimate how much $SO_2F_2$, TFE, PESF, and PDES were present at the end of the reaction. This information was used to calculate PESF and PDES yields, PESF/PDES mole ratios (selectivity), and percent TFE consumed. The reactor was cleaned with water and acetone and dried in an oven at 100° C. in preparation for the next run.

TABLE 1

| Example # | Catalyst (Conc. Wt % in Solvent) | Solvent (E) | TFE/SO$_2$F$_2$ Molar Charge Ratio | Rxn Temp (° C.) | Rxn Time (hrs) | % TFE Consumed | % Yield PESF* | % Yield Sulfone* | PESF/Sulfone Mole Ratio |
|---|---|---|---|---|---|---|---|---|---|
| C1 | KF (~6.7%) anhyd, sd | Diglyme (7.2) | 0.73 | 50–100 | 5 | NR | NA | NA | NA |
| C2 | CsF (7.0%) anhyd | Diglyme (7.2) | 1.09 | 64–100 | 12 | 63% | 52% | 8.4% | 6.2 |
| C3 | KF (6.4%) anhyd, sd | Diglyme (7.2) | 0.67 | 81–91 | 14.5 | NR | NA | NA | NA |
| 4 | KF (4.2%) anhyd, sd; 18-C-6 (8.4%) | CH$_3$CN (36.6) | 0.94 | 90–102 | 5.5 | 67% | 54% | 4.7% | 11.4 |
| C5 | (Me$_2$N)2C=C(NMe$_2$)$_2$ | None | 0.74 | 42–55 | 9.0 | NR | NA | NA | NA |
| 6 | KF (3.9%) anhyd, sd; 18-C-6 (7.9%); Bu$_4$N$^+$—N(SO$_2$CF$_3$)$_2$ (3.9%) | CH$_3$CN (36.6) | 1.38 | 70 | 9.0 | ~41% | ~50% | 3.7% | 13.5 |
| C7 | KF (7.4%) anhyd, sd | CH$_3$CN (36.6) | 1.14 | 85–90 | 6.2 | NR | NA | NA | NA |
| C8 | NaF (1.7%) DB-18-C-6 (6.3%) | o-DCB (10.1) | 1.01 | 100 | 8.0 | NR | NA | NA | NA |
| C9 | Me$_3$N (1.1%) | FC-43 (1.9) | 1.14 | 100 | 4.0 | NR | NA | NA | NA |
| C10 | KF (3.2%) anhyd, sd; 18-C-6 (6.4%) | Diglyme (7.2) | 0.97 | 70–75 | 5.5 | NR | NA | NA | NA |
| C11 | PROTON-SPONGE ™ (4.0%); Et$_3$N—3HF (1.0%) | Diglyme (7.2) | 0.97 | 100 | 5.5 | NR | NA | NA | NA |
| C12 | CsF (8.1%) anhyd | CH$_3$CN (36.6) | 0.78 | 100 | 21.5 | 41% | 29% (37% based on TFE) | 1.8% | 16.1 |
| C13 | KF (4.8%) anhyd, sd; Tetraglyme (32.3%) | CH$_3$CN (36.6) | 0.94 | 100 | 21.0 | NR | NA | NA | NA |
| 14 | KF (2.5%) anhyd, sd; 18-C-6 (5.0%) | Sulfolane (42.2) | 0.98 | 100 | 3.5 | 104% | 44% | 29% | 1.5 |
| 15 | KF (2.9%) anhyd, sd; 18-C-6 (5.7%) | DMPU (36.6) | 0.93 | 100–120 | 5.5 | 81% | 51% | 12% | 4.2 |
| 16 | KF (2.4%) anhyd, sd; 18-C-6 (4.8%) | PC (66.1) | 0.97 | 100 | 5.0 | 70% | 39% | 14.5% | 2.6 |
| 17 | KF (3.8%) anhyd, sd; DC-18-C-6 (7.7%) | CH3CN (36.6) | 1.00 | 100 | 5.0 | 51% | 42% | 4.3% | 9.7 |
| C18 | CsF (6.4%) ARC anhyd | Diglyme (7.2) | 1.13 | 85 | 6.5 | Very Low Conversion | NA | NA | NA |
| 19 | KF (3.2%) anhyd, sd; 18-C-6 (6.3%) | DMF (38.2) | 1.15 | 100 | 3.5 | 83% | 61% | 17.4% | 3.5 |
| 20 | KF (2.1%) anhyd, sd; 18-C-6 (4.2%) | DMF/FC-104 | 1.12 | 100 | 4.0 | 90.2% | 70.4% | 15.6% | 4.5 |
| C21 | KF (6.7%) wet, sd | DMF (38.2) | 1.22 | 80–113 | 15.0 | 38% | 33% | 7% | 4.7 |
| C22 | KF (6.2%) anhyd, sd | DMF (38.2) | 0.93 | 82–111 | 14.0 | 75% | 48% | 11% | 4.3 |
| 23 | KF (2.1%) anhyd, sd; 18-C-6 (1%) | DMF/FC-104 | 1.31 | 88–101 | 7.0 | 80% | 61% | 22% | 2.7 |
| 24 | KF (2.1%) anhyd, sd; 18-C-6 (0.5%) | DMF/FC-104 | 1.02 | 90–120 | 14.0 | 86% | 64% | 12% | 5.3 |

TABLE 1-continued

| Example # | Catalyst (Conc. Wt % in Solvent) | Solvent (E) | TFE/ $SO_2F_2$ Molar Charge Ratio | Rxn Temp (° C.) | Rxn Time (hrs) | % TFE Consumed | % Yield PESF* | % Yield Sulfone* | PESF/Sulfone Mole Ratio |
|---|---|---|---|---|---|---|---|---|---|
| 25 | KF (3.6%) wet, sd; 18-C-6 (1.7%) wet | DMA (38.3) | 0.62 | 100–101 | 11.0 | 67% | 36% (58% based on TFE) | 2.7% | 13.3 |
| 26 | KF (3.2%) anhyd, sd; 18-C-6 (1.6%) | DMA (38.3) | 0.99 | 100 | 8.0 | 73% | 53% | 10% | 5.3 |
| C27 | KF (3.0%) anhyd, sd; $Me_4N^+$ —$C(SO_2CF_3)_3$ (6.0%) | DMF (38.2) | 1.08 | 90–100 | 8.0 | >42%*** | >37.5%*** | >4%*** | 9.1 |
| C28 | KI (3.7%) wet | DMF (38.2) | 1.11 | 82–85 | 6.0 | NR | NR | NR | NA |
| C29 | KI (3.5%) anhyd 18-C-6 (5.1%) | DMF (38.2) | 1.09 | 81–82 | 7.0 | NR | NR | NR | NA |

NR is no reaction
* % Yield of PESF and Sulfone is based on the amount of $SO_2F_2$ charged.
** In each case, a total of 32 mL of solvent was employed.
*** Minor product losses in exit gases not measured.
sd=spray-dried, E=dielectric constant, wet means reactor was loaded in ambient air and reactants and catalysts were unprotected from atmospheric moisture.

Comparative Examples C1, C2, C3, C7, C12, C18, C21, and C22 illustrate the relatively low catalytic activity of metal fluoride catalysts alone (with no crown ether co-catalyst).

Comparative Example C13 illustrates the relatively low catalytic activity of metal fluoride catalysts when combined with acyclic polyether co-catalyst.

Comparative Example C27 illustrates the relatively low catalytic activity of metal fluoride catalysts when combined with a quaternary ammonium co-catalyst.

Comparative Examples C21–C22 and Examples 25–26 illustrate the detrimental effect of water on catalytic activity.

Comparative Examples C28–C29 illustrate the very low catalytic activity of KI, even when a crown ether co-catalyst is employed.

Examples 19 and 20 illustrate the advantages in PESF yield and selectivity when a highly fluorinated co-solvent is employed.

Examples 20, 23, and 24 illustrate how catalytic activity decreases as the concentration of crown ether co-catalyst is lowered.

Comparative Examples C8 and C10 illustrate the relatively low catalytic activity obtained with metal fluoride/crown ether catalyst mixtures if solvents of low dielectric constant are employed.

Comparative Examples C5, C9, and C11 show that $(Me_2N)_2C=C(NMe_2)_2$, $Me_3N$ and PROTON-SPONGE™/$Et_3N$-3HF are ineffective catalysts.

Examples 4, 14, 15, 16, 17, 19, 20, 23, 24, and 26 illustrate the improved conversions, rates, and product yields obtained with anhydrous metal fluoride catalyst/crown ether co-catalyst mixtures of the present invention when high dielectric constant solvents and their mixtures with highly fluorinated co-solvents are employed.

Example 6 demonstrates that further addition of an anhydrous quaternary ammonium salt to the catalyst mixture of the present invention has little or no impact on catalyst performance and offers no process advantages or disadvantages.

Figure 2:
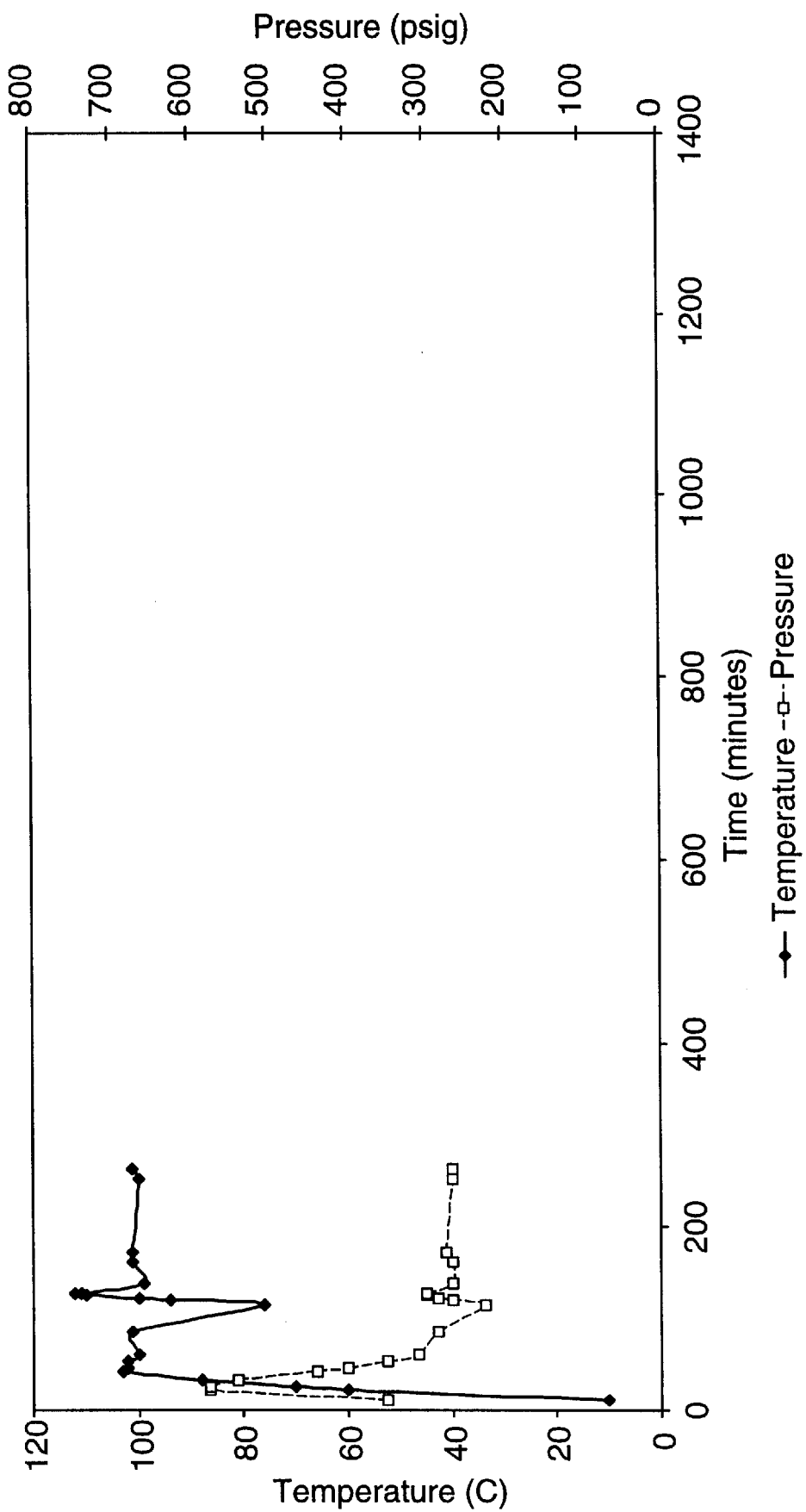
FIG. 2 is a graph of reaction temperature and pressure versus time for Example 19.
Figure 3:
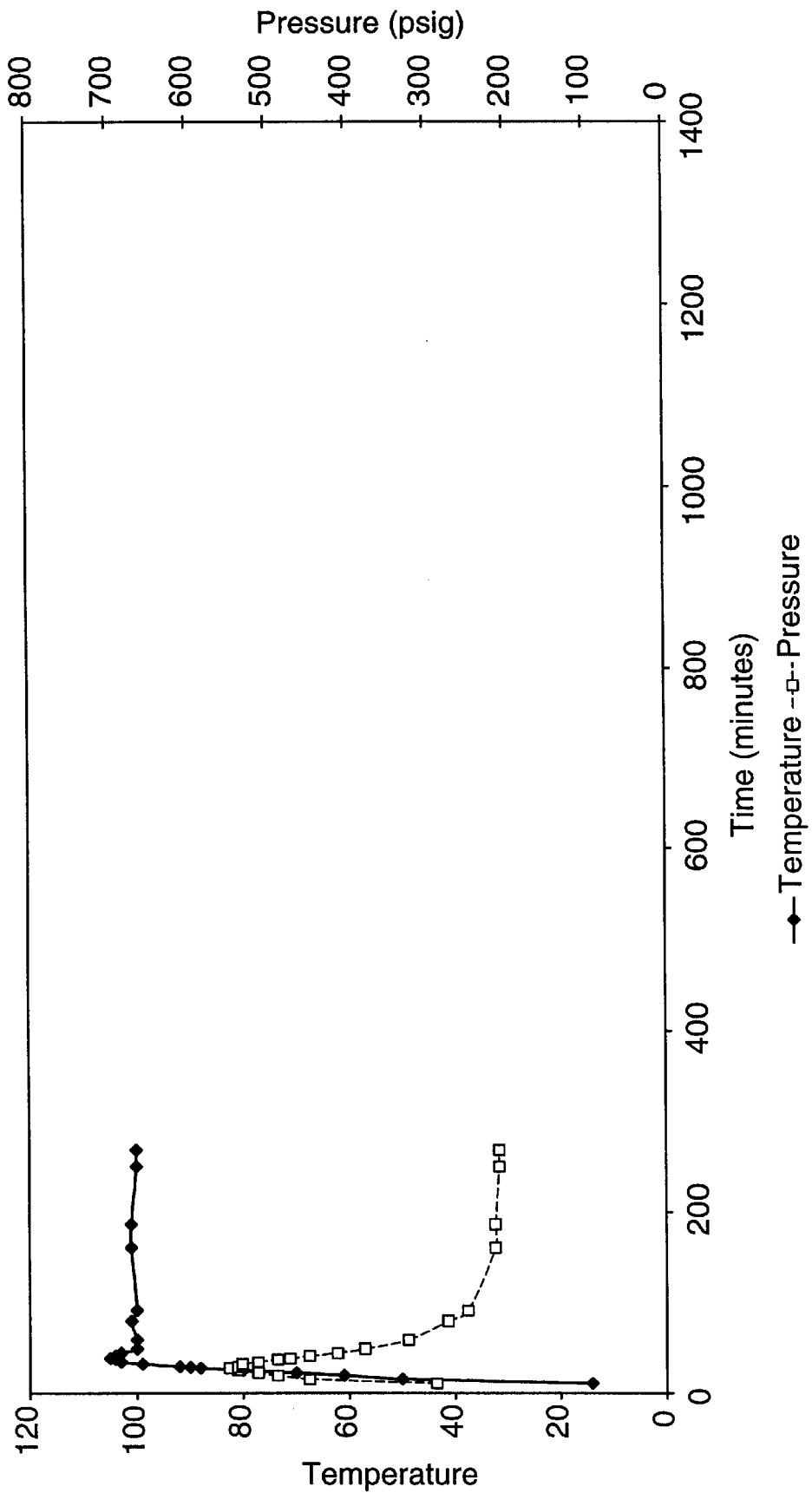
FIG. 3 is a graph of reaction temperature and pressure versus time for Example 20.
Figure 4:
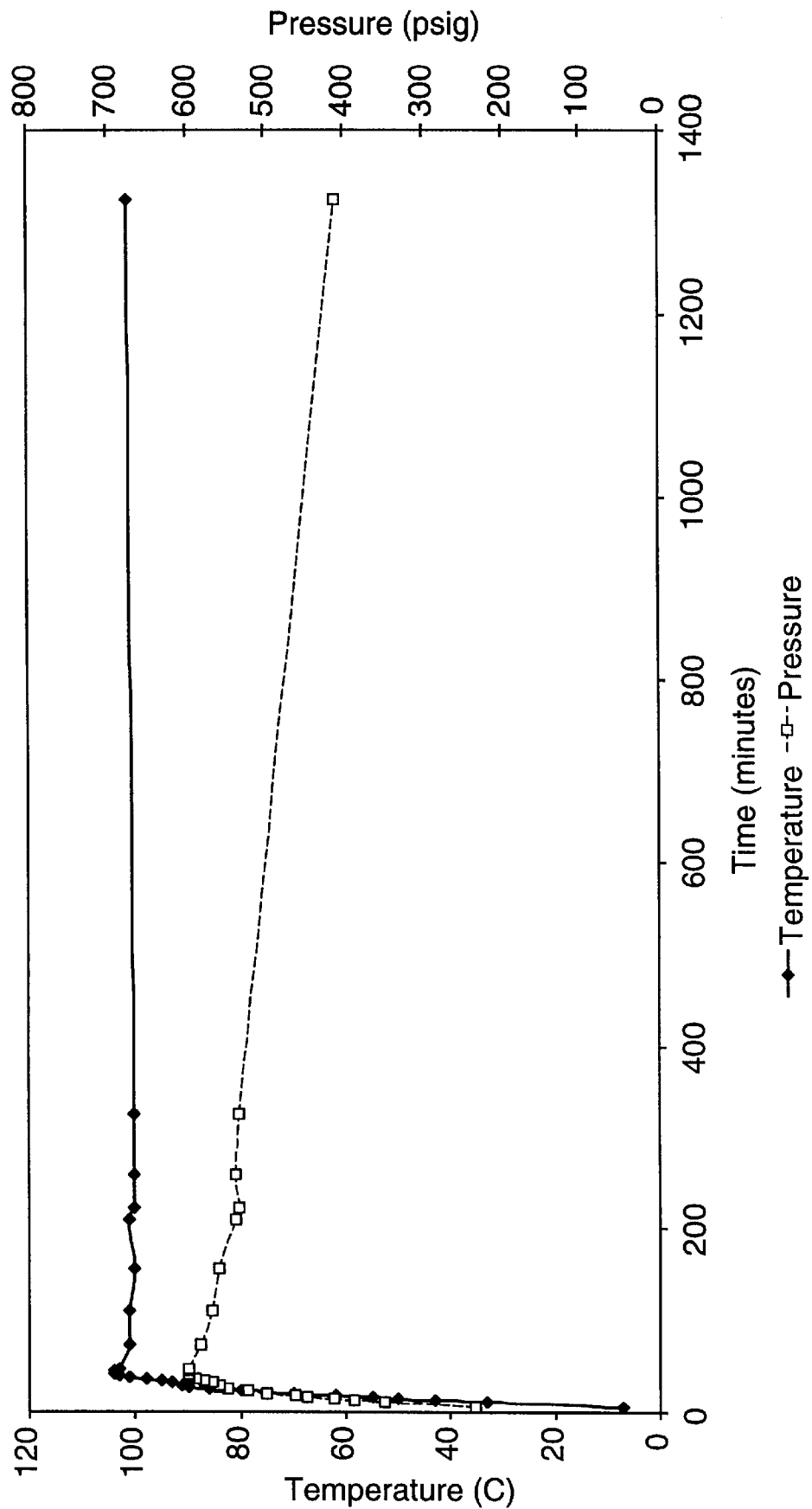
FIG. 4 is a graph of reaction temperature and pressure versus time for Example C12.
Figure 5:
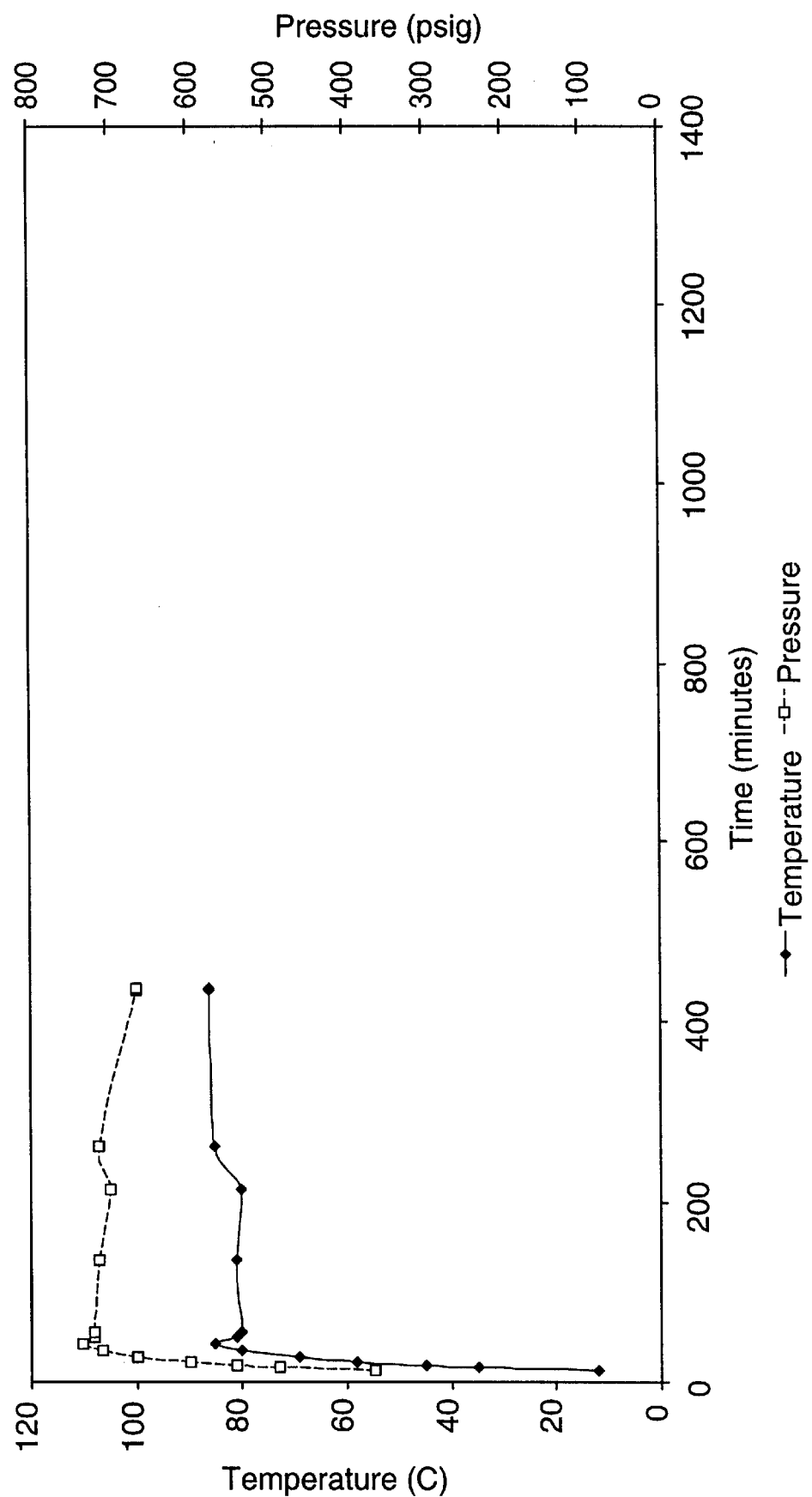
FIG. 5 is a graph of reaction temperature and pressure versus time for Example C18.
Figure 6:
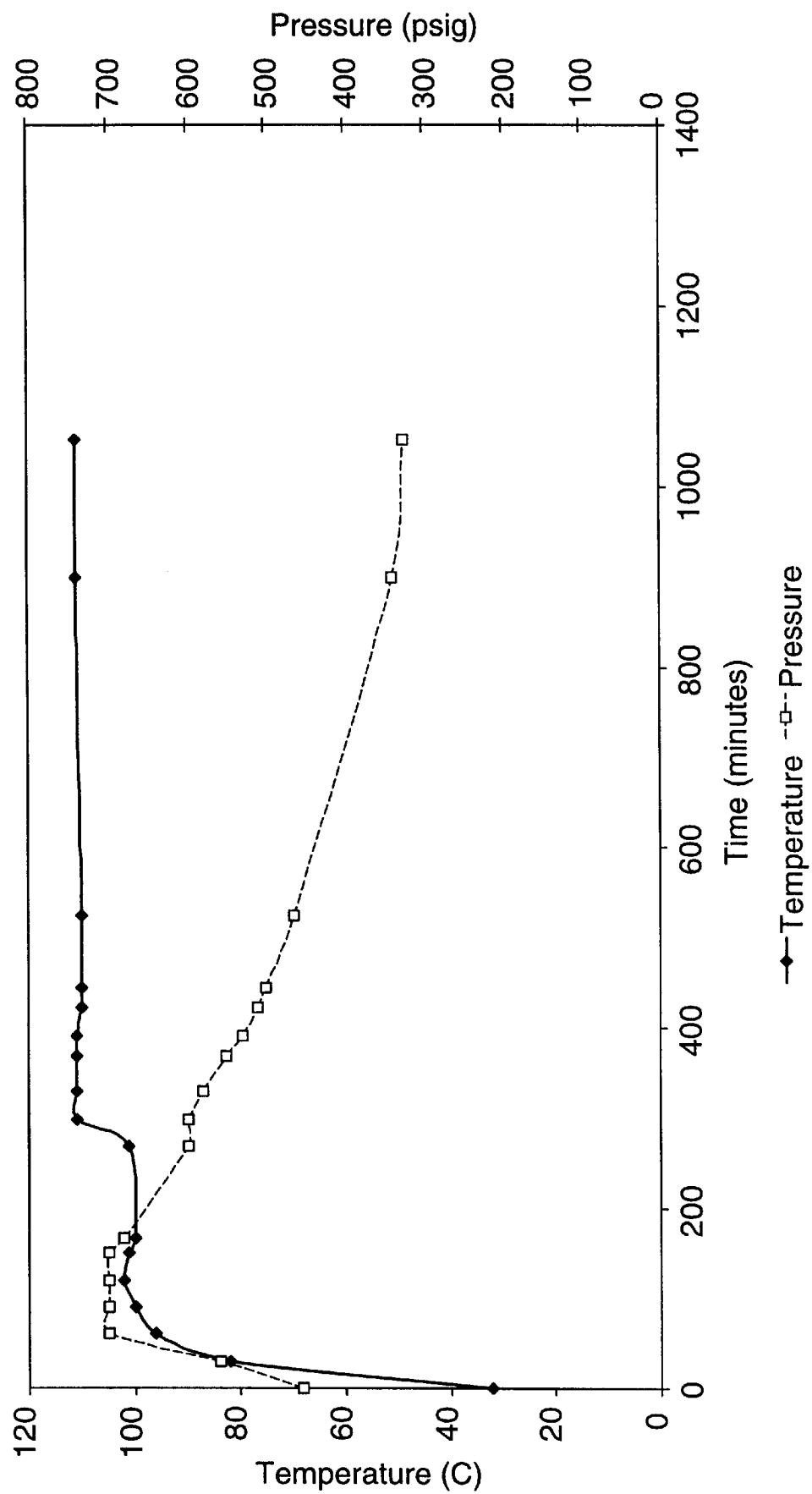
FIG. 6 is a graph of reaction temperature and pressure versus time for Example C22.
Figure 7:
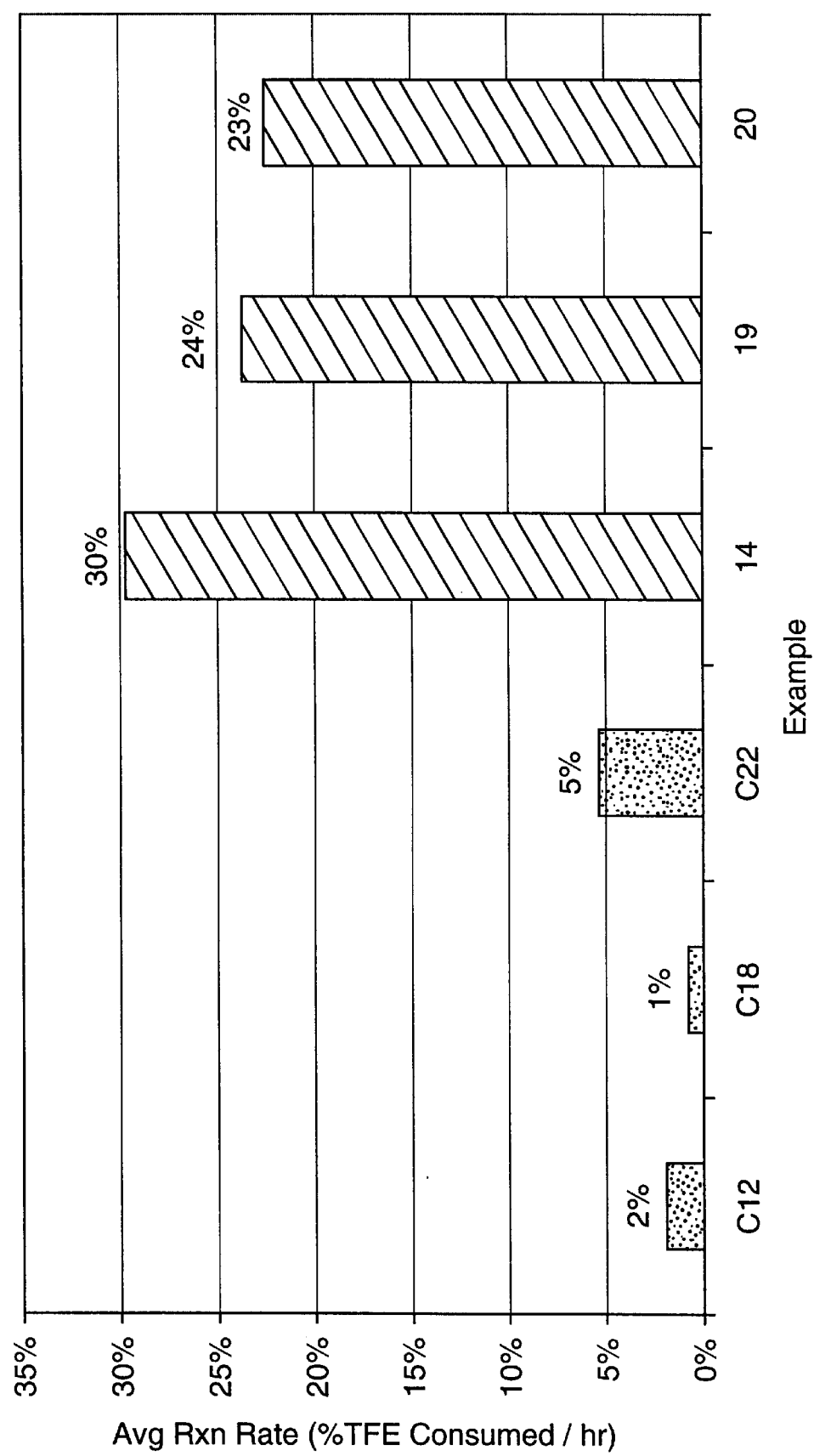
FIG. 7 is a bar graph of the average rates of reaction expressed as percent conversion of TFE per unit time for Examples 14, 19, and 20 and Comparative Examples C12, C18, and C22.

A further illustration of the improved reactivity of the two-part catalysts of the present invention versus one-part CsF or KF catalysts is provided in the comparative plots of reactor pressure and temperature versus reaction time (FIGS. 1 to 6) for examples C12 (FIG. 4), C18 (FIG. 5), C22 (FIG. 6), 14 (FIG. 1), 19 (FIG. 2), and 20 (FIG. 3) and a bar graph comparing the average rates of TFE conversion (FIG. 7). It is apparent from the plots in FIGS. 1 to 6 that the two-part catalysts of the present invention produce a relatively rapid drop in reactor pressure over time (from conversion of gaseous TFE and $SO_2F_2$ reagents to liquid products), whereas the comparative one-part metal fluoride catalysts produce a much slower drop in reactor pressure at comparable or higher temperatures. The rate of pressure drop in these examples is a direct measure of the rate of reaction of TFE with $SO_2F_2$ to produce PESF and/or PDES. The relatively high activity of the two-part catalysts of the present invention compared to known one-part metal fluoride catalysts is also apparent from the bar graph in FIG. 7 showing average rates of TFE conversion. The latter rates were calculated by talking the percent TFE conversion measured at the end of the reaction and dividing by the total reaction time in hours.

Examples 27–46

The catalytic reaction of the present invention was run in two different modes. The "pre-charge" mode was used for Examples 27–28 and the "co-feed" mode was used for the Examples 29–47. These Examples were organized into five series where each series was run with one batch of solvent/catalyst mixture.

A 1-gallon (3.8 liter) volume, stirred tank reactor with a 400-psig-(2.86 MPa) rupture disk setting and a connection to a 375-psi (2.59 MPa) nitrogen supply and a vacuum was used. The reactor had a water jacket for temperature control. A controller was used to operate a steam-water ratio valve to control the jacket temperature.

TFE was supplied through a carbon absorption column to remove the limonene inhibitor.

At the end of an example, crude PESF and PDES product was collected by venting the reactor to an evacuated cylinder placed in a dry ice bath. The cold cylinder pulled and condensed the unreacted TFE and $SO_2F_2$ and the product PESF and PDES from the reactor. As the flow to the product cylinder tended to stall out at 25 to 50 psia (172 to 344 kPa) a second evacuated product cylinder was needed to get a good material balance for each example. To start each series of examples the reactor was rinsed and boiled out at about 100° C. with DI water twice, then with acetone at about 100° C., and finally, with inert perfluorinated fluid, at about 100° C. After each rinse and boil-out the reactor was evacuated to evaporate as much water as possible. After the rinse and boil-out procedure was completed, the reactor was charged with the next solvent/catalyst mixture from a 2.25 liter stainless steel cylinder. After the completion of a series, the reactor was drained, cleaned out as before, and then charged with the next batch of solvent/catalyst.

A summary of the solvent/catalyst batches used in the 5 series of examples is listed in Table 2.

TABLE 2

Solvent/Catalyst Batches

| Series No. | Number of Catalytic Examples per Series | Description of Solvent/Catalyst Mixture |
|---|---|---|
| 1 | 7 | 1.890 Kg DMF, 125 g. 18-crown-6 (anhyd), 62.5 g. KF (anhyd) |
| 2 | 3 | 0.944 Kg DMF, 62.5 g. 18-crown-6 (anhyd), 31.2 g. KF (anhyd), 1.909 Kg FC-1 |
| 3 | 5 | 0.944 Kg DMF, 62.5 g. 18-crown-6 (anhyd), 31.2 g. KF (anhyd), 1.845 Kg FC43 |
| 4 | 2 | 0.944 Kg DMF, 62.5 g. 18-crown-6 (anhyd), 31.2 g. KF (anhyd), 1.773 Kg FC3255 |
| 5 | 3 | 1.888 Kg DMF, 62.5 g. 18-crown-6 (anhyd), 31.2 g. KF (anhyd) |

Precharge Mode

The first two catalytic reactions were carried out in the precharge mode. In this mode of operation, the reactor was heated to the run temperature and then charged with all the $SO_2F_2$ used in the reaction. Next, TFE was charged to raise the pressure to the desired run pressure and the reaction was started. As the reaction proceeded, the pressure dropped as reactants were consumed. Each time the pressure dropped by 10 psi (69 kPa) more TFE was fed to the reactor to bring the pressure back to the target run pressure. When the prescribed amount of TFE had been fed, the TFE feed was stopped and the reactor pressure was allowed to drop as the reaction went to completion.

All reactions following Example 28 were done in the co-feed mode at 240 psia (1.65 MPa).

Co-feed Mode

In the co-feed reaction mode the initially evacuated, preheated reactor was first charged to approximately half the desired run pressure with $SO_2F_2$, and then TFE was added to bring the pressure up to the run pressure, usually 240 psia (1.65 MPa). As the reaction proceeds, $SO_2F_2$ and TFE were alternately added to maintain the reactor pressure at the desired run pressure until the total feed of reactants for that run had been reached. Because the two feed gases had differing solubilities in the solvent/catalyst mixture, $SO_2F_2$ was usually added in about 10 psi (69 KPa) intervals, and TFE was usually added in about 13 psi (90 kPa) intervals. When all $SO_2F_2$ and TFE for a run had been added, the pressure was allowed to run down until the reaction reached completion.

At the end of each run a cylinder sample of headspace gas, and a liquid sample from each product cylinder were collected for GC analysis. The liquid samples were held in dry ice to prevent them from evaporating. Still, a small amount of TFE and $SO_2F_2$ were lost from the first sample cylinder from each example because even at −78° C. the material collected in the first product cylinder has a vapor pressure of 20 to 50 psia (138 to 345 kPa).

Samples were analyzed on an HP 5890 Gas Chromatograph equipped with a packed 9'×⅛" (275 cm×0.32 cm) stainless steel Supelco 60/80 Carbopack C column, and a thermal conductivity detector. The oven was ramped from 0 to 250° C. at 15° C. per minute with no initial isothermal hold. Low boiling samples were analyzed by cold-injection using a 10-microliter syringe pre-chilled to dry-ice temperatures in a plastic bag to prevent frosting. Gas samples were introduced using a disposable 1 ml plastic syringe. Area percent responses by GC were assumed proportional to mass percent concentrations from the product samples.

A summary of conditions and results for these Examples are shown in Table 3 below.

TABLE 3

| | Run Data Example | | | | | | | | | |
|---|---|---|---|---|---|---|---|---|---|---|
| | 27 | 28 | 29 | 30 | 31 | 32 | 33 | 34 | 35 | 36 |
| Temperature, ° C. | 100 | 80 | 72 | 70 | 70 | 50 | 100 | 70 | 70 | 70 |
| Pressure, psia | 330 | 340 | 280 | 280 | 240 | 240 | 280 | 240 | 240 | 240 |
| (MPa) | (2.28) | (2.34) | (1.93) | (1.93) | (1.65) | (1.65) | (1.93) | (1.65) | (1.65) | (1.65) |
| Solvent/Catalyst Charge (Series #) | 1 | 1 | 1 | 1 | 1 | 1 | 1 | 2 | 2 | 2 |
| Feed Method | Precharge | Precharge | Co-Feed | Co-Feed | Co-Feed | Co-Feed | Co-Feed | Co-Feed | Co-Feed | Co-Feed |
| TFE/$SO_2F_2$ Feed Ratio | 1 | 1 | 1.1 | 1.1 | 1 | 1 | 1 | 1 | 1.1 | 1.2 |
| Gas Feed Rate, g/min avg. | | | 1.65 | 1.91 | 1.34 | 0.79 | 1.99 | 1.87 | 1.25 | 0.88 |
| Run Length, hr. | 5 | 12 | 14 | 15 | 20 | 29 | 9 | 17 | 20 | 28 |
| % TFE Consumed | 97 | 97 | 99 | 96 | 97 | 88 | 98 | 97 | 95 | 94 |
| % $SO_2F_2$ Consumed | 86 | 78 | 87 | 88 | 76 | 70 | 70 | 78 | 83 | 89 |
| PESF Yield (recov'd, S basis), % | 63 | 64 | 68 | 68 | 58 | 59 | 55 | 70 | 73 | 75 |
| PDES Yield (recov'd, S basis) | 20 | 15 | 19 | 20 | 18 | 12 | 16 | 7 | 11 | 14 |
| Combined Yield (recov'd, S basis) | 83 | 78 | 87 | 87 | 76 | 71 | 71 | 78 | 84 | 90 |
| PDES/PESF (mole ratio) | 0.31 | 0.23 | 0.28 | 0.29 | 0.31 | 0.21 | 0.30 | 0.11 | 0.15 | 0.19 |

TABLE 3-continued

| | | | | | | | | | | |
|---|---|---|---|---|---|---|---|---|---|---|
| Total SO$_2$F$_2$ Charge (g) | 682 | 752 | 753 | 751 | 750 | 752 | 751 | 752 | 754 | 756 |
| Total TFE Charge (g) | 671 | 738 | 812 | 810 | 736 | 737 | 736 | 737 | 814 | 888 |

| | Run Data Example | | | | | | | | | |
|---|---|---|---|---|---|---|---|---|---|---|
| | 37 | 38 | 39 | 40 | 41 | 42 | 43 | 44 | 45 | 46 |
| Temperature, ° C. | 70 | 70 | 70 | 70 | 70 | 70 | 70 | 70 | 70 | 70 |
| Pressure, psia | 240 | 240 | 240 | 280 | 240 | 240 | 240 | 240 | 240 | 240 |
| (MPa) | (1.65) | (1.65) | (1.65) | (1.93) | (1.65) | (1.65) | (1.65) | (1.65) | (1.65) | (1.65) |
| Solvent/Catalyst Charge (Series #) | 3 | 3 | 3 | 3 | 3 | 4 | 4 | 5 | 5 | 5 |
| Feed Method | Co-Feed | Co-Feed | Co-Feed | Co-Feed | Co-Feed | Co-Feed | Co-Feed | Co-Feed | Co-Feed | Co-Feed |
| TFE/SO$_2$F$_2$ Feed Ratio | 1.2 | 1 | 1.2 | 1.2 | 1.2 | 1.10 | 1.2 | 1.2 | 1.1 | 1.3 |
| Gas Feed Rate, g/min avg. | 2.13 | 1.68 | 1.15 | 1.17 | 0.67 | 1.98 | 1.06 | 3.03 | 1.98 | 1.47 |
| Run Length, hr. | 14 | 18 | 22 | 28 | 33 | 15 | 24 | 9 | 11 | 16 |
| % TFE Consumed | 98 | 98 | 98 | 96 | 98 | 97 | 98 | 98 | 99 | 99 |
| % SO$_2$F$_2$ Consumed | 88 | 79 | 91 | 91 | 89 | 82 | 91 | 84 | 81 | 92 |
| PESF Yield (recov'd, S basis), % | 80 | 69 | 74 | 75 | 74 | 74 | 74 | 67 | 64 | 65 |
| PDES Yield (recov'd, S basis) | 10 | 11 | 17 | 17 | 15 | 10 | 18 | 18 | 17 | 27 |
| Combined Yield (recov'd, S basis) | 89 | 80 | 91 | 91 | 89 | 84 | 92 | 85 | 81 | 92 |
| PDES/PESF (mole ratio) | 0.12 | 0.16 | 0.23 | 0.22 | 0.20 | 0.14 | 0.24 | 0.28 | 0.27 | 0.42 |
| Total SO$_2$F$_2$ Charge (g) | 753 | 702 | 752 | 753 | 476 | 751 | 752 | 753 | 750 | 751 |
| Total TFE Charge (g) | 885 | 688 | 884 | 885 | 560 | 810 | 884 | 886 | 809 | 958 |

In Examples 27 and 28, the catalytic reaction appears to reach equilibrium at long times with 1 to 2 percent of the TFE and somewhat more of the SO$_2$F$_2$ charged remaining unreacted. The run length in Table 3 is the time required to get 99 percent of the way to equilibrium based on feeds charged and the drop in pressure as the reaction runs down.

In some series, the reaction slowed down with each consecutive catalytic reaction using the same catalyst/solvent system. For example, in the five run series, Examples 37 through 41, the reaction time (i.e., run time) for Example 37 was 14 hours and the reaction time for Example 41 was 33 hours.

As Table 3 indicates, a continuous feed process can be used to achieve high conversions and high yields of PESF and PDES while maintaining relatively low system pressure.

The catalyst system may also be reused multiple times.

Various modifications and alterations of this invention will be apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

What is claimed is:

1. A catalytic process for the preparation of perfluoroethanesulfonyl fluoride and/or perfluorodiethylsulfone, in a rector comprising the steps of:
   a) reacting in the presence of a two-part catalyst system in a polar aprotic organic solvent:
      i) tetrafluoroethylene (TFE), and
      ii) sulfuryl fluoride (SO$_2$F$_2$);
      wherein said two-part catalyst system comprises a metal fluoride, and a crown ether; and
   b) recovering perfluoroethanesulfonyl fluoride or perfluorodiethylsulfone or a mixture thereof.

2. The catalytic process according to claim 1, wherein said metal fluoride is an alkali metal fluoride.

3. The catalytic process according to claim 2, wherein said alkali metal fluoride is selected from the group consisting of NaF, KF, and CsF.

4. The catalytic process according to claim 1, wherein a sufficient amount of inhibitor is present to prevent free radical polymerization of the tetrafluoroethylene.

5. The catalytic process according to claim 1, wherein said crown ether is selected from the group consisting of 18-crown-6, dibenzo-18-crown-6, dicyclohexano-18-crown-6, and dibenzo-24-crown-8.

6. The catalytic process according to claim 1, wherein said polar aprotic organic solvent is selected from the group consisting of: acetonitrile, dimethylformamide, dimethylacetamide, sulfolane, dimethylsulfoxide, propylene carbonate, 1,3-dimethylimidazolidin-2-one, 1,3-dimethyl-2-oxohexahydropyrimidine, gamma-butyrolactone, nitromethane, 1-methyl-2-pyrrolidinone, dimethylsulfone, and hexamethylphosphoroamide.

7. The catalytic process according to claim 1, wherein said polar aprotic organic solvent has a dielectric constant at room temperature greater than 25.

8. The catalytic process according to claim 1, wherein the mixture of two-part catalyst and solvent(s) is reused multiple times.

9. The catalytic process according to claim 1, wherein the percent tetrafluoroethylene consumed is greater than 85% and the mole ratio of perfluorodiethylsulfone:perfluoroethane sulfonyl fluoride in the final product is less than 0.35.

10. The catalytic process according to claim 1, wherein essentially all water has been excluded.

11. The catalytic process according to claim 1, wherein the maximum reactor pressure is less than 350 psia (62 kPa).

12. The catalytic process according to claim 1, wherein the maximum reactor temperature is less than 120° C.

13. The catalytic process according to claim 1, wherein the tetrafluoroethylene and the SO$_2$F$_2$ are continuously charged to the reactor.

14. The catalytic process according to claim 1, wherein the SO$_2$F$_2$ is precharged batch-wise to the reactor and the tetrafluoroethylene is fed continuously to the reactor.

15. The catalytic process according to claim 1, wherein the SO$_2$F$_2$:tetrafluoroethylene mole ratio is greater than one.

16. The catalytic process according to claim 15, wherein the excess SO$_2$F$_2$ is recovered and recycled.

17. The catalytic process according to claim 1, wherein the $SO_2F_2$:tetrafluoroethylene mole ratio is less than one.

18. The catalytic process according to claim 1, wherein said process further comprises combining a fluorinated co-solvent with said polar aprotic organic solvent, wherein the fluorinated co-solvent and the polar aprotic organic solvent are immiscible.

19. The catalytic process according to claim 18, wherein said fluorinated co-solvent is selected from the group consisting of: perfluorocarbons, perfluorinated tertiary amines, perfluorinated ether-amines, cyclic and acyclic perfluorinated ethers, perfluoropolyethers, hydrofluorocarbons, and bisperfluoroalkylsulfones.

20. The catalytic process according to claim 18, wherein said fluorinated co-solvent is perfluorodiethylsulfone.

21. A catalytic process for the preparation of a perfluoroethanefluoroalkanesulfone comprising the steps of:
  a) reacting in the presence of a two-part catalyst system in a polar aprotic organic solvent:
    i) tetrafluoroethylene, and
    ii) a fluoroalkanesulfonyl fluoride;
      wherein said two-part catalyst system comprises a metal fluoride and a crown ether; and
  b) recovering the perfluoroethanefluoroalkanesulfone.

* * * * *

UNITED STATES PATENT AND TRADEMARK OFFICE
CERTIFICATE OF CORRECTION

PATENT NO.    : 6,580,006 B1
DATED         : June 17, 2003
INVENTOR(S)   : Lamanna, William M.

It is certified that error appears in the above-identified patent and that said Letters Patent is hereby corrected as shown below:

Column 7,
Line 41, delete "2-methyloxyethyl" and insert in place thereof -- 2-methoxyethyl --

Column 9,
Table 1, "Example 1," third column, delete "CH3CN" and insert in place thereof -- $CH_3CH$ --

Column 12,
Line 47, delete "talking" and insert in place thereof -- taking --
Line 55, delete "29-47" and insert in place thereof -- 29-46 --

Columns 13 and 14,
Table 3, delete "Example" under "Run Data" and insert in place thereof in the first column, preceding "27"

Column 15,
Line 54, delete "rector" and insert in place thereof -- reactor; --

Signed and Sealed this

First Day of June, 2004

JON W. DUDAS
*Acting Director of the United States Patent and Trademark Office*